United States Patent
Isaka et al.

(10) Patent No.: US 9,851,334 B2
(45) Date of Patent: Dec. 26, 2017

(54) GAS SENSOR ASSEMBLING METHOD AND GAS SENSOR ASSEMBLING APPARATUS

(71) Applicant: NGK INSULATORS, LTD., Nagoya-shi, Aichi (JP)

(72) Inventors: Kenji Isaka, Nagoya (JP); Hiroyuki Tanaka, Nagoya (JP); Kenji Kato, Handa (JP)

(73) Assignee: NGK INSULATORS, LTD., Nagoya (JP)

( * ) Notice: Subject to any disclaimer, the term of this patent is extended or adjusted under 35 U.S.C. 154(b) by 192 days.

(21) Appl. No.: 14/638,648

(22) Filed: Mar. 4, 2015

(65) Prior Publication Data
US 2015/0253298 A1    Sep. 10, 2015

(30) Foreign Application Priority Data

Mar. 10, 2014 (JP) .................. 2014-046329

(51) Int. Cl.
*G01R 3/00* (2006.01)
*G01N 33/00* (2006.01)
(Continued)

(52) U.S. Cl.
CPC ...... *G01N 33/0009* (2013.01); *G01M 15/102* (2013.01); *G01N 27/4071* (2013.01);
(Continued)

(58) Field of Classification Search
CPC .......... G01N 27/4071; G01N 27/4078; G01N 33/0009; G01M 15/02
(Continued)

(56) References Cited

U.S. PATENT DOCUMENTS 4,019,974 A * 4/1977 Weyl .................. G01N 27/4062
                                                                204/428
4,505,807 A * 3/1985 Yamada ............... G01N 27/417
                                                                204/412
(Continued)

FOREIGN PATENT DOCUMENTS

EP      0343533 A2   11/1989
JP      1-264729 A   10/1989
(Continued)

OTHER PUBLICATIONS

The Extended European Search Report for the corresponding European patent application No. 15157946.3 dated Jul. 16, 2015.
(Continued)

*Primary Examiner* — Paul D Kim
(74) *Attorney, Agent, or Firm* — Global IP Counselors, LLP (57) ABSTRACT

A gas sensor assembling method includes a step for placing an element dummy such that it has a longitudinal direction in a vertical direction, wherein the cross-sectional shape of the dummy is similar to the cross-sectional shape of a sensor element, a step for fitting a through hole in an annularly-mounted member to the dummy from above vertically, wherein the through hole included in the annularly-mounted member corresponds to the cross-sectional shape of the sensor element, a step for fitting a tubular member to an outer periphery of the annularly-mounted member from above vertically, an step for placing the sensor element in contact with an upper end portion of the dummy on a single straight line, and an step for descending the dummy downwardly vertically for descending the sensor element and fitting the through hole in the annularly-mounted member to the sensor element.

18 Claims, 8 Drawing Sheets

(51) Int. Cl.
*G01M 15/10* (2006.01)
*G01N 27/407* (2006.01)

(52) U.S. Cl.
CPC .... *G01N 27/4078* (2013.01); *Y10T 29/49002* (2015.01); *Y10T 29/53261* (2015.01)

(58) Field of Classification Search
USPC .......... 29/592.1, 594, 609.1; 73/23.21, 866.5
See application file for complete search history.

(56) References Cited

U.S. PATENT DOCUMENTS

| | | | | |
|---|---|---|---|---|
| 4,591,423 A † | 5/1986 | Kato | | |
| 5,451,748 A * | 9/1995 | Matsuzaki | ............. | H05B 3/141 |
| | | | | 219/543 |
| 5,728,289 A * | 3/1998 | Kirchnavy | ........... | G01N 27/404 |
| | | | | 204/409 |
| 6,510,728 B2 * | 1/2003 | Matsuo | ................ | G01N 27/407 |
| | | | | 204/424 |
| 6,658,916 B2 * | 12/2003 | Donelon | .............. | G01N 27/407 |
| | | | | 204/424 |
| 6,691,553 B2 * | 2/2004 | Holleboom | ........ | G01N 27/4077 |
| | | | | 73/23.32 |
| 9,032,779 B2 * | 5/2015 | Otsubo | .............. | G01N 27/4077 |
| | | | | 73/23.31 |
| 2002/0017128 A1 | 2/2002 | Shirai | | |
| 2005/0022361 A1 † | 2/2005 | Matsuo | | |
| 2014/0102170 A1 | 4/2014 | Kato | | |

FOREIGN PATENT DOCUMENTS

| | | | |
|---|---|---|---|
| JP | 06-226557 A † | 8/1994 |
| JP | 4173465 A | 8/2008 |
| JP | 2011-117831 A | 6/2011 |
| WO | 2013/005491 A1 | 1/2013 |

OTHER PUBLICATIONS

The Third Party Observation for the corresponding European application No. 15157946.3 issued on May 16, 2017.

\* cited by examiner
† cited by third party

GAS SENSOR ASSEMBLING METHOD AND GAS SENSOR ASSEMBLING APPARATUS

BACKGROUND OF THE INVENTION

Field of the Invention

The present invention relates to a method for assembling a gas sensor including a ceramic sensor element and to an assembly apparatus for use in assembling the same.

Description of the Background Art

Conventionally, there have been well known gas sensors having sensor elements formed from an oxygen-ion conductive solid electrolyte ceramic, such as zirconia ($ZrO_2$), as devices for determining the concentrations of predetermined gas components in measurement gas, such as combustion gasses and exhaust gasses in internal combustion engines such as automobile engines.

Such gas sensors generally include a sensor element (detection element) with an elongated plate shape which is made of a ceramic, wherein the sensor element is secured by a plurality of ceramic supporters which are ceramic insulators and by powder compacts made of ceramics such as talc which are embedded between the ceramic supporters, in a hollow portion of a metal housing and a cylindrical inner tube secured thereto through welding, so that the powder compacts provide hermetic sealing. There have been already well known methods and apparatuses for preferably assembling such gas sensors (refer to International Publication WO 2013/005491 and Japanese Patent Application Laid-Open No. 2005-37372).

International Publication WO 2013/005491 discloses a method which enables annularly-mounted members, which are the plural members to be annularly mounted on a sensor element, to be annularly mounted without fail even when the sensor element has warpage and, also, there is a smaller dimensional tolerance between the sensor element and the annularly-mounted members.

With the method disclosed in International Publication WO 2013/005491, the annularly-mounted members are annularly mounted to the sensor element, from its end portion provided with an opening portion for introducing measurement gas into the inside of the element. Therefore, if this method is applied to a sensor element which is covered with a protection film (protection layer) over the surface of this end-portion-side of the sensor element, this induces malfunctions such as injuries and exfoliations of the protection film, which is unpreferable.

On the other hand, Japanese Patent Application Laid-Open No. 2005-37372 discloses a method for fabricating a gas sensor including a detection element which is not covered with a protection layer at its one end portion. However, in the fabrication method disclosed in Japanese Patent Application Laid-Open No. 2005-37372, annularly-mounted members are temporarily annularly mounted to a pin member with a shape similar to that of the detection element and, thereafter, the pin member is pulled out therefrom to realize a state where the plural annularly-mounted members are stacked, and, then, the detection element is inserted into the stacked annularly-mounted members. This induces the problem that the annularly-mounted members are liable to displace, when the pin member is pulled out therefrom, and when the detection element is inserted thereinto.

SUMMARY OF THE INVENTION

The present invention relates to a method for assembling a gas sensor including a sensor element made of a ceramic, and an assembling apparatus for use in the same assembling and, more particularly, is directed to a method and an apparatus for annularly mounting a member to an outer periphery of a sensor element.

According to the present invention, there is provided a gas sensor assembling method including the steps of a) placing an element dummy having a shape similar to that of a sensor element such that it has a longitudinal direction in a vertical direction, the sensor element having an elongated shape mainly composed of a ceramic; b) fitting a through hole in an annularly-mounted member to the element dummy from above vertically, the annularly-mounted member having a disk shape or a cylindrical shape, and the through hole having a shape corresponding to a cross-sectional shape of the sensor element; c) fitting a tubular body to an outer periphery of the annularly-mounted member from above vertically; d) placing the sensor element in contact with an upper end portion of the element dummy on a single straight line; and e) descending the element dummy downwardly vertically for descending the sensor element and fitting the through hole in the annularly-mounted member to the sensor element.

Accordingly, in assembling the gas sensor, the annularly-mounted member is consistently in the state of being annularly mounted to the element dummy or the sensor element. This can preferably inhibit the occurrence of malfunctions that the annularly-mounted member is displaced to make it impossible to assemble the sensor element therein.

Preferably, when the sensor element is provided with a protection film on a surface of its one end, in the step d), the sensor element is placed such that another end of the sensor element which is not provided with the protection film is supported by the element dummy.

This enables preferably assembling the gas sensor without injuring the protection film.

Further, in another aspect of the present invention, a gas sensor assembling apparatus includes: an element dummy having a shape similar to that of a sensor element, the sensor element having an elongated shape mainly composed of a ceramic; a dummy placing component for placing the element dummy such that it has a longitudinal direction in a vertical direction; an annularly-mounted member fitting component for fitting a through hole in an annularly-mounted member to the element dummy from above vertically, the annularly-mounted member having a disk shape or a cylindrical shape, and the through hole having a shape corresponding to a cross-sectional shape of the sensor element; a tubular-body fitting component for fitting a tubular body to an outer periphery of the annularly-mounted member from above vertically; an element placing component for placing the sensor element in contact with an upper end portion of the element dummy on a single straight line; and an element fitting component for descending the element dummy downwardly vertically for descending the sensor element and fitting the through hole in the annularly-mounted member to the sensor element.

Therefore, in assembling the gas sensor, the annularly-mounted member is consistently in the state of being annularly mounted to the element dummy or the sensor element. This can preferably inhibit the occurrence of malfunctions that the annularly-mounted member is displaced to make it impossible to assemble the sensor element therein.

Preferably, when the sensor element is provided with a protection film on a surface of its one end, the element placing component places the sensor element, such that another end of the sensor element which is not provided with the protection film is supported by the element dummy.

This enables preferably assembling the gas sensor without injuring the protection film.

Accordingly, it is an object of the present invention to provide a gas sensor assembling method which enables preferably annularly mounting annularly-mounted members to a sensor element.

These and other objects, features, aspects and advantages of the present invention will become more apparent from the following detailed description of the present invention when taken in conjunction with the accompanying drawings.

DESCRIPTION OF THE PREFERRED EMBODIMENTS

<Configuration of Gas Sensor>

Figure 1:
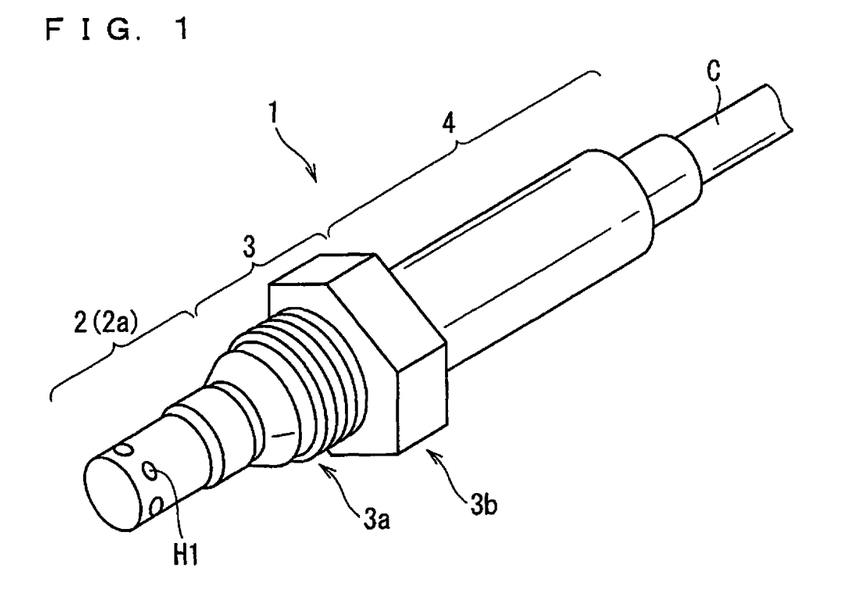
FIG. 1 is a perspective view of an external appearance of a gas sensor (more specifically, the main body thereof) to be assembled, according to the present preferred embodiment.
Figure 2:
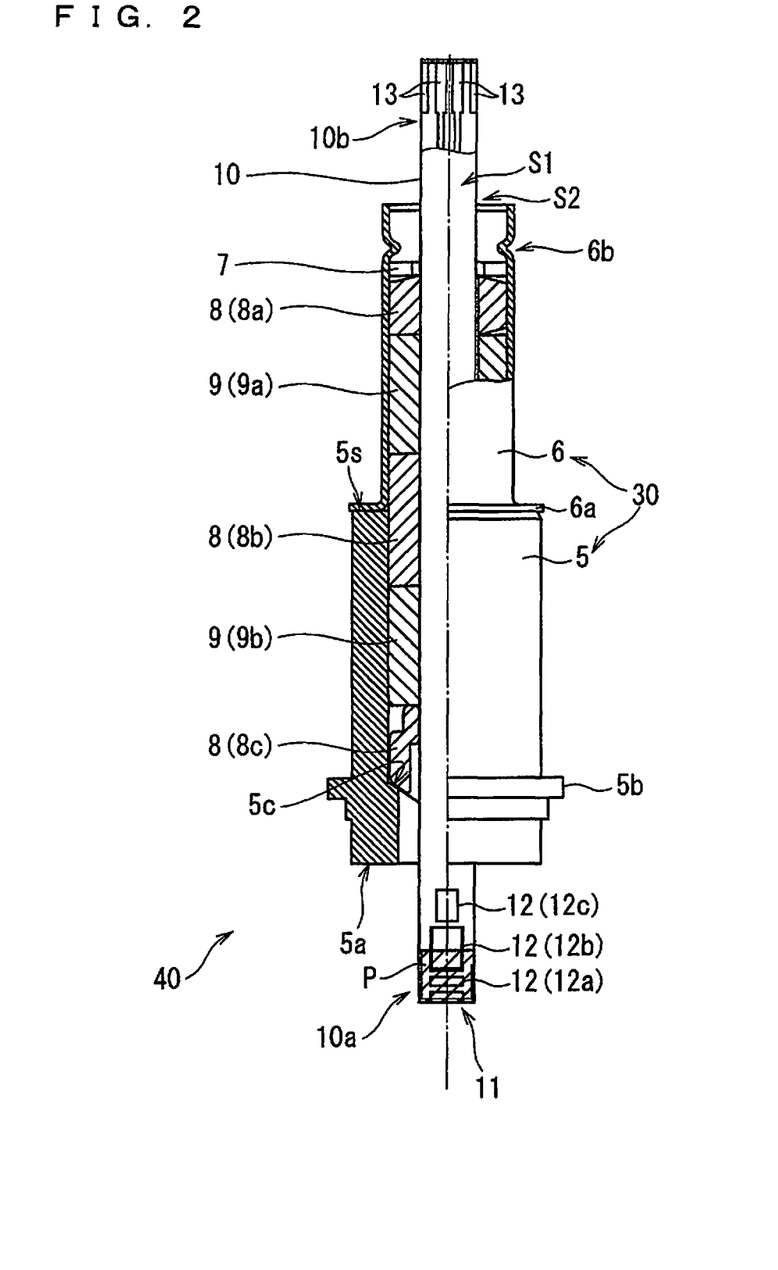
FIG. 2 is a partial cross-sectional view illustrating a main structure inside this gas sensor 1.

FIG. 1 is an external perspective view of a gas sensor (more specifically, a main body thereof) 1 to be assembled in this embodiment. FIG. 2 is a partial cross-sectional view showing a main configuration of the inside of the gas sensor 1. In this embodiment, the gas sensor 1 serves to detect a predetermined gas component (such as NOx) with a sensor element 10 (FIG. 2) included therein.

The sensor element 10 is an elongated cylindrical or thin-plate like member including as a main constituent material an element body of oxygen-ion conductive solid electrolyte ceramic such as zirconia. The sensor element 10 has a configuration in which a gas inlet, an internal space, and the like are provided on a first tip 10a side and various electrodes and a wiring pattern are provided on the surface and inside of the element body. In the sensor element 10, a detection gas introduced into the internal space is reduced or decomposed in the internal space, to thereby generate oxygen ions. The gas sensor 1 determines the concentration of the gas component based on a fact that an amount of oxygen ions flowing inside an element is proportional to the concentration of the gas component in a detection gas. In FIG. 2, the surface facing the front surface is referred to as a main surface S1 of the sensor element 10, and the surface that is perpendicular to the main surface S1 and extends along the longitudinal direction is referred to as a side surface S2. Further, the surface of the sensor element 10 is covered with a protection film P, over a predetermined range therein from the first tip 10a in the longitudinal direction (see FIG. 2). The protection film P is a porous film with a thickness of about 10 micrometers to 2000 micrometers and is made of $Al_2O_3$, for example. The protection film P is also referred to as a heat-shock protection layer. However, the range over which the protection film P is formed thereon in FIG. 2 is merely illustrative, and, in actual, the range over which it is formed can be determined as appropriate, depending on the concrete structure of the sensor element 10.

The outside of the gas sensor 1 is mainly formed of a first cover 2, a fixing bolt 3, and a second cover 4.

The first cover 2 is an approximately cylindrical exterior member that protects a portion of the sensor element 10 that comes into direct contact with the detection gas in use, which is specifically the first tip 10a including a gas inlet 11 and a closed space 12 (buffer space 12a, first internal space 12b, and second internal space 12c). For easy understanding, FIG. 2 and the following diagrams show that the gas inlet 11 and the closed space 12 (buffer space 12a, first internal space 12b, and second internal space 12c) are formed in the main surface S1. In actuality, those parts are not exposed in the main surface S1 but are each provided inside the sensor element 10 except for the gas inlet 11 being open at the first tip 10a which is the lowermost end of the sensor element 10 in FIG. 2.

More specifically, the first cover 2 has a double-layer structure of an outside cover 2a and an inside cover (not shown). Each of the outside cover 2a and inside cover has a circular bottom on one side and has a plurality of through holes through which a gas passes in the side portion. FIG. 1 illustrates through holes H1 provided in the outside cover 2a, which are merely an example. The position and number of through holes arranged may be appropriately determined in consideration of how a measurement gas flows into the first cover 2.

The fixing bolt 3 is an annular member to be used when the gas sensor 1 is fixed at a measurement position. The fixing bolt 3 includes a threaded bolt portion 3a and a held portion 3b to be held when the bolt portion 3a is screwed. The bolt portion 3a is screwed with a nut provided at a position at which the gas sensor 1 is mounted. For example, the bolt portion 3a is screwed with a nut portion provided in the car exhaust pipe, whereby the gas sensor 1 is fixed to the exhaust pipe such that the first cover 2 side thereof is exposed in the exhaust pipe.

The second cover 4 is a cylindrical member that protects other part of the gas sensor 1. A cable C for electrically connecting the gas sensor 1 and a drive controller (not shown) extends from the end of the second cover 4.

FIG. 2 shows the internal configuration of the gas sensor 1, more specifically, the configuration of the gas sensor 1 except for the first cover 2, fixing bolt 3, and second cover 4 shown in FIG. 1.

As shown in FIG. 2, inside the gas sensor 1, a washer 7, three ceramic supporters 8 (8a, 8b, and 8c), and two powder compacts 9 (9a and 9b) are each annularly mounted to the part of the sensor element 10 except for the first tip 10a, which includes the gas inlet 11 and the like, and a second tip 10b, which includes terminals 13 for connection with the cable C, such that the sensor element 10 is positioned about the axis. The ceramic supporter 8 is a ceramic insulator. Meanwhile, the powder compact 9 is obtained by shaping ceramic powders such as talc. In the following description, the washer 7, the ceramic supporters 8, and the powder compacts 9 are collectively referred to as annularly-mounted members, in some cases.

Figure 3:
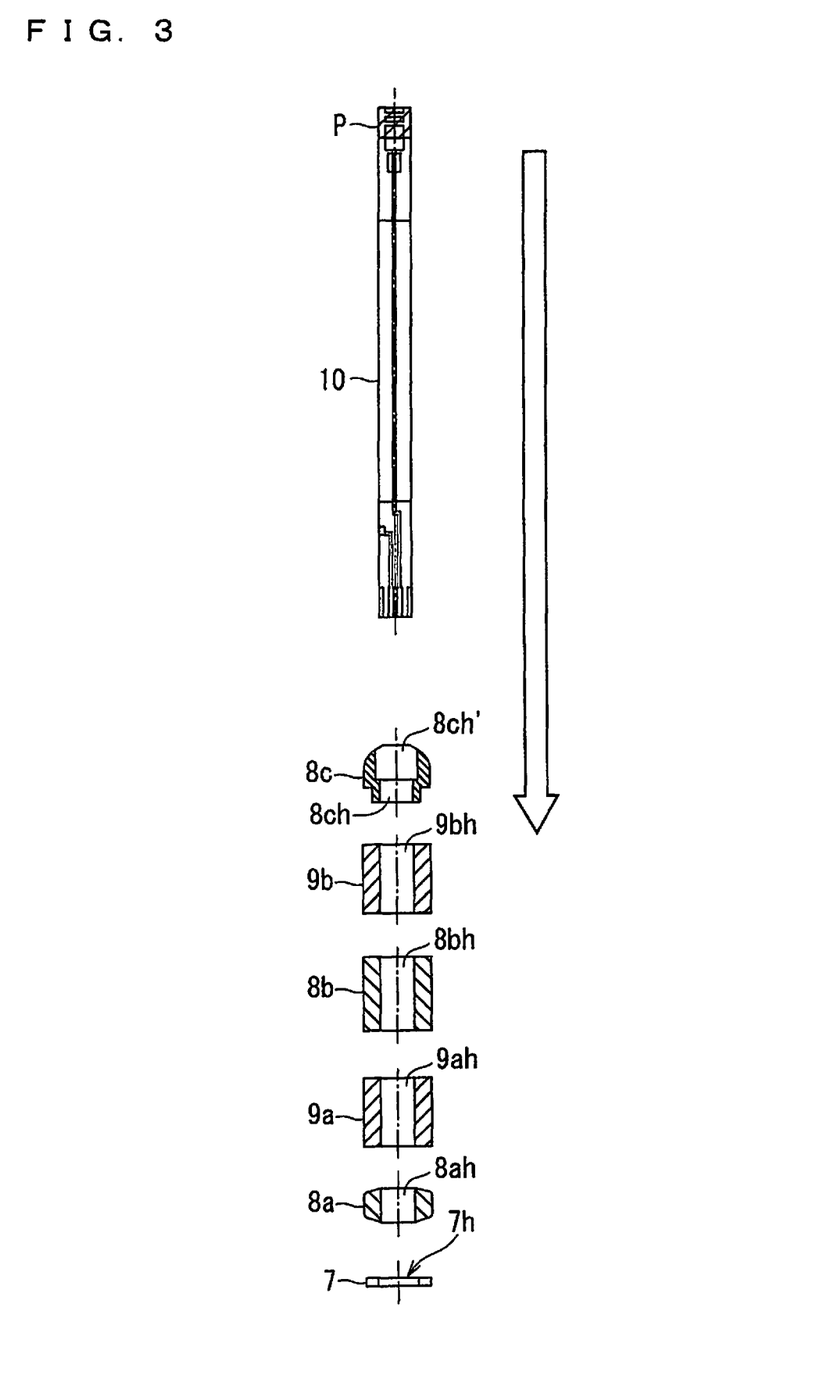
FIG. 3 is a view schematically illustrating the state where a washer 7, ceramic supporters 8 and powder compacts 9 are annularly mounted to a sensor element 10.

FIG. 3 is a view schematically showing an appearance where the washer 7, the ceramic supporters 8 (8a, 8b and 8c) and the powder compacts 9 (9a and 9b) are annularly mounted to the sensor element 10.

As shown in FIG. 3, in outline, this annular mounting is realized by inserting the end portion (the second tip 10b) of the sensor element 10 which is not provided with the protection film P, into the ceramic supporter 8c, the powder compact 9b, the ceramic supporter 8b, the powder compact 9a, the ceramic supporter 8a and the washer 7, in the mentioned order. Each member has a disc shape or cylindrical shape. For annularly mounting as described above, a circular through hole 7h is provided at the axis center position of the washer 7, and through holes 8ah, 9ah, 8bh, 9bh, and 8ch having a rectangular shape corresponding to the cross-sectional shape of the sensor element 10 are provided in the ceramic supporter 8a, powder compact 9a, ceramic supporter 8b, powder compact 9b, and ceramic supporter 8c, respectively. Those through holes are fitted with the sensor element 10, so that the members are each annularly mounted to the sensor element 10. The part of the ceramic supporter 8c that is opposed to the through hole 8ch is an opening 8ch' open wider than the through hole 8ch. The washer 7, ceramic supporters 8, and powder compacts 9 are coaxially arranged.

From the viewpoint of securing airtightness, the through holes of the ceramic supporters 8 and the through holes of the powder compacts 9 are configured such that a difference with a design cross-sectional size of the sensor element 10 is 0.25 to 0.35 mm and a dimensional tolerance is 0.1 mm. Meanwhile, the through hole 7h of the washer 7 is provided so as to have a difference with the design cross-sectional size of the sensor element 10 of at least 1 mm or more and 1.3 mm or less. The washer 7, ceramic supporters 8, and powder compacts 9 are configured to have a difference in outside diameter value of approximately 0.35 mm at a maximum.

As shown in FIG. 2, a cylindrical tubular body (inner tube welded product) 30, which is obtained by integrating a housing 5 being a ceramic cylindrical member and an inner tube 6 being a metallic cylindrical member, is annularly mounted to the outer peripheries of the washer 7, the ceramic supporters 8 (8a, 8b and 8c) and the power compacts 9 (9a, 9b and 9c). In the following description, the configuration in which the tubular body 30 is annularly mounted in such a manner is referred to as an assembled product 40.

The tubular body 30 is formed by integrally welding a bend 6a bent outwardly, which is included in one end of the inner tube 6, to an end surface 5s of the housing 5. The housing 5 and inner tube 6 have substantially the same inside diameter and are connected coaxially. An inside diameter of the tubular body 30 is set to be larger than designed values of the maximum outside diameters of respective annularly-mounted members.

The housing 5 is provided with a tapered portion 5c at one end side of the inside thereof. The inner tube 6 is provided with a concave portion 6b which is recessed inwardly, at a position just above the washer 7. With these tapered portion 5c and concave portion 6b, the washer 7, the ceramic supporters 8 (8a, 8b and 8c) and the powder compacts 9 (9a and 9b), which are annularly mounted to the sensor element 10, are engaged with the inside of the tubular member 30. Due to this engagement, sealing is provided in a region between the first tip 10a of the sensor element 10, which includes the gas inlet 11 and the like, and the second tip 10b thereof, which includes the terminals 13 for connection with the cable C and the like, inside the assembled product 40. This secures the airtightness between the measurement gas space and the reference gas space.

The assembled product 40 having the aforementioned structure is covered with the first cover 2, fixing bolt 3, and second cover 4, finally to form the gas sensor 1. Specifically, the first cover 2 is connected to a tubular portion 5a at the tip of the housing 5. The fixing bolt 3 is annularly mounted to the outer periphery of the housing 5 so as to come into contact with a projection (a flange portion) 5b. Moreover, the second cover 4 is mounted so as to be fitted into an annular groove between the fixing bolt 3 and housing 5, which is formed through the above annular mounting.

The above-mentioned configuration allows the gas sensor 1 to completely cut off the atmosphere (atmosphere in the first cover 2) around the first tip 10a of the sensor element 10 from the outside atmosphere in a state in which the gas sensor 1 is mounted at a predetermined position. This allows for accurate measurement of the concentration of a target gas component in the detection gas.

(The Procedure for Assembling the Assembled Member)

Figure 4:
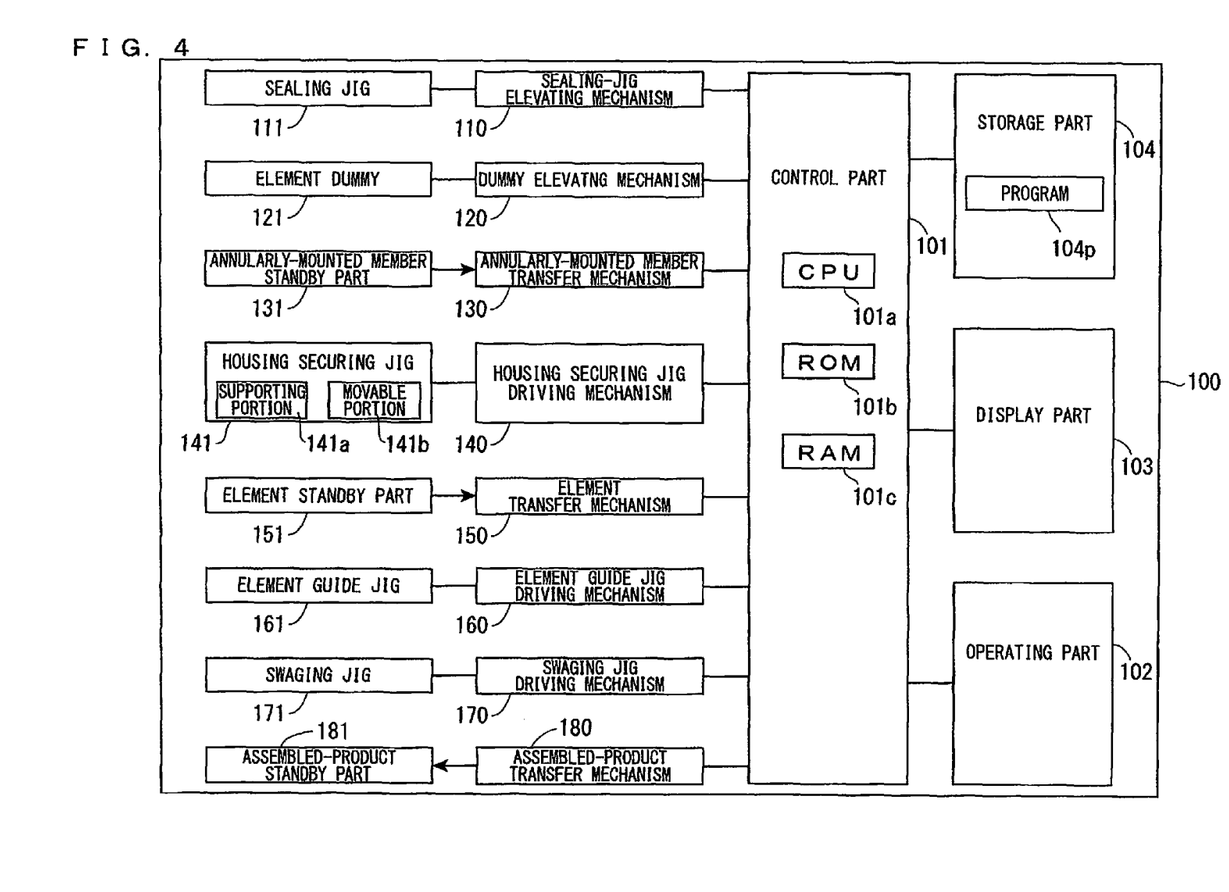
FIG. 4 is a block diagram schematically illustrating the structure of an assembling apparatus 100.

Next, there will be described the procedure for assembling the assembled product 40, which is performed in the present preferred embodiment. FIG. 4 is a block diagram schematically illustrating the structure of an assembling apparatus 100 for performing this assembling.

The assembling apparatus 100 includes a control part 101 for controlling the overall operations of the assembling apparatus 100, wherein the control part 101 is constituted by a CPU 101a, a ROM 101b, a RAM 101c and the like. The assembling apparatus 100 further includes an operating part 102 being an input interface which is constituted by switches, buttons, a touch panel and the like for generating various types of execution commands to the assembling apparatus 100, a display part 103 constituted by a display and measuring instruments for displaying various types of operation menus and operation states of the assembling apparatus 100, and a storage part 104 which stores an operation program 104p for the assembling apparatus 100, and operation condition data and the like which are not illustrated. In the assembling apparatus 100, the operation program 104p is executed by the control part 101, so that a series of assembling operations which will be described later are performed through automatic processing.

As components for performing actual assembling operations, the assembling apparatus 100 further includes a sealing-jig elevating mechanism 110 for performing operations for elevating a sealing jig 111, a dummy elevating mechanism 120 for performing operations for elevating an element dummy 121, an annularly-mounted member transfer mechanism 130 for transferring annularly-mounted members from an annularly-mounted member standby part 131 to a predetermined position, a housing securing jig driving mechanism 140 for operating a housing securing jig 141, an element transfer mechanism 150 for transferring the sensor element 10 from an element standby part 151 to a predetermined position, an element guide jig driving mechanism 160 for operating an element guide jig 161, a swaging jig driving mechanism 170 for operating a swaging jig 171, and an assembled-product transfer mechanism 180 for transferring the assembled product 140 to an assembled-product standby part 181.

FIGS. 5 to 8 are schematic cross-sectional views of the assembled product 40 in process of assembling, for explaining the procedure for assembling the assembled product 40 using this assembling apparatus 100. Further, in FIGS. 5 to 8, the vertically-upward direction is designated as a Z-axis positive direction.

Figure 5A:
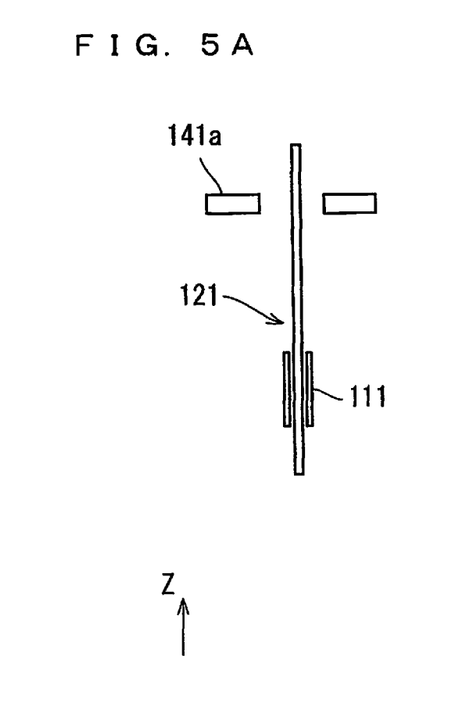
FIGS. 5A, 5B and 5C, 6A, 6B and 6C, 7A and 7B, and 8A and 8B are schematic cross-sectional views each illustrating a state halfway through assembling of an assembled member 40.

At first, as illustrated in FIG. 5A, an element dummy 121 is inserted through the sealing jig 111.

The sealing jig 111 is a cylindrical member having openings at its opposite ends. The sealing jig 111 is placed in such a way as to have a longitudinal direction in the vertical direction at a predetermined position (an initial position) in the assembling apparatus 100 and, also, is adapted to freely move up and down in the vertical direction through the sealing jig elevating mechanism 110 which is not illustrated in FIGS. 5A, 5B and 5C. Further, the outer diameter of the sealing jig 111 which is normal to the longitudinal direction thereof is made smaller than the outer diameters of the washer 7, the ceramic supporters 8 and the powder compacts 9. The inner diameter of the sealing jig 111 is made larger than the largest sizes of the through holes in the washer 7, the ceramic supporters 8 and the powder compacts 9. This enables the sealing jig 111 to support the annularly-mounted members, from therebelow, at the upper end side of the sealing jig 111 in the vertical direction.

The element dummy 121 is a member with an elongated plate shape similar to that of the sensor element 10, wherein the cross-sectional shape of the element dummy 121 which is normal to its longitudinal direction is similar to the cross-sectional shape of the sensor element 10 in the longitudinal direction. The element dummy 121 is adapted to freely move up and down in the vertical direction, through the dummy elevating mechanism 120 which is not illustrated in FIGS. 5A, 5B and 5C. However, the element dummy 121 is not necessarily required to be formed from a ceramic as the sensor element 10 and can be also formed from an appropriate material in consideration of the durability and the wear resistance. The element dummy 121 is formed to have a thickness and a width which are smaller than the through holes in the ceramic supporters 8, and the powder compacts 9 but are slightly larger than those of the sensor element 10. The element dummy 121 is inserted through the inside of the sealing jig 111 from vertically below the sealing jig 111 and is placed in such a way as to have a longitudinal direction in the vertical direction, through the dummy elevating mechanism 120. At this time, the dummy elevating mechanism 120 functions as dummy placing means for placing the element dummy 121 such that it has a longitudinal direction in the vertical direction. In this case, the element dummy 121 is inserted thereinto, up to a position which makes the distance from its vertically-upper end portion to the vertically-upper end portion of the sealing-jig 111 larger than the sum of the thicknesses of all the annularly-mounted members.

After the element dummy 121 has been inserted therein as described above, subsequently, the annularly-mounted members are annularly mounted onto the element dummy 121 and, subsequently, the tubular body 30 is annularly mounted thereto.

Figure 5B:
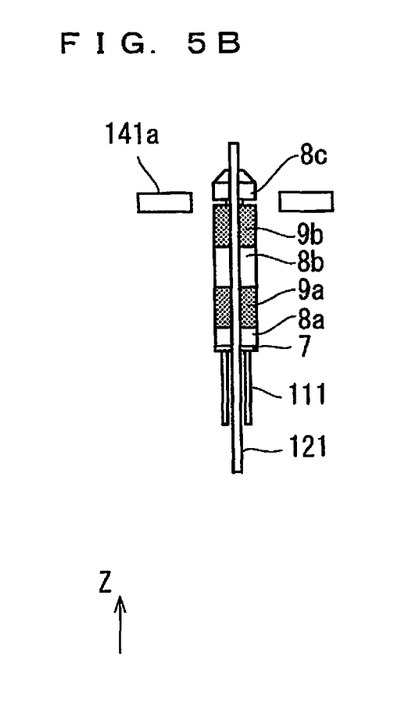
Figure 5C:
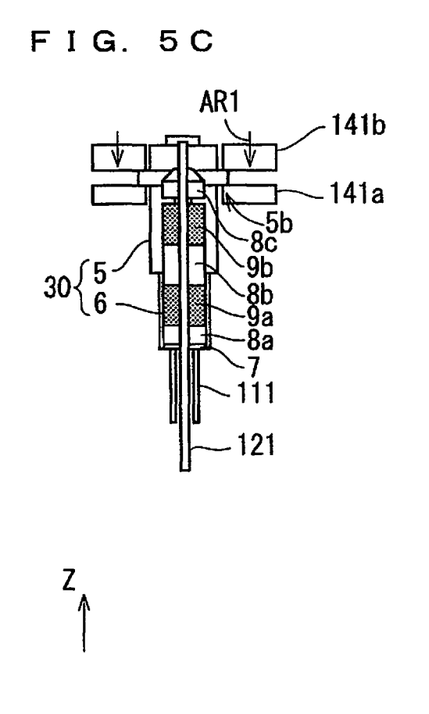

At first, the annularly-mounted member transfer mechanism 130 which is not illustrated in FIGS. 5A, 5B and 5C transfers the annularly-mounted members which have been preliminarily carried therein from the outside of the apparatus and have been on standby at the annularly-mounted member standby part 131, to the position of the element dummy 121, in the order of the washer 7, the ceramic supporter 8a, the powder compact 9a, the ceramic supporter 8b, the powder compact 9b and the ceramic supporter 8c. Further, the annularly-mounted member transfer mechanism 130 fits the through holes in the respective members to the element dummy 121. This realizes a state where the respective annularly-mounted members which have been fitted to the element dummy 121 in order are supported from therebelow vertically, by the upper end portion of the sealing jig 111, as illustrated in FIG. 5B. At this time, the annularly-mounted member transfer mechanism 130 functions as annularly-mounted member fitting means for fitting the through holes in the annularly-mounted members to the element dummy 121.

After completing the aforementioned annular mounting, subsequently, the annularly-mounted member transfer mechanism 130 transfers the tubular body 30 which has been similarly carried therein from the outside of the apparatus and has been on standby at the annularly-mounted-member standby part 131, to above the element dummy 121 onto which the annularly-mounted members have been annularly mounted. Further, the annularly-mounted member transfer mechanism 130 descends the tubular body 30 at such an attitude that the inner tube 6 is oriented downwardly in the vertical direction and, further, fits it onto the outer peripheries of the annularly-mounted members. This realizes a state where the annularly-mounted members, onto which the tubular body 30 has been fitted, are supported from therebelow vertically, by the upper end portion of the sealing jig 111, as illustrated in FIG. 5C. At this time, the annularly-mounted member transfer mechanism 130 functions as tubular-member fitting means for fitting the tubular member 30 to the outer peripheries of the annularly-mounted members.

More specifically, the annularly-mounted member transfer mechanism 130 descends the tubular body 30, until the projection 5b of the housing 5 comes into contact with a supporting portion 141a which constitutes the housing securing jig 141, from above. Due to this contacting, the tubular body 30 is supported by the supporting portion 141a from therebelow vertically. In other words, the height position of the tubular body 30 in the vertical direction is defined by the supporting portion 141a. Further, after the projection 5b is supported by the supporting portion 141a from therebelow vertically, in such a manner, the housing securing-jig driving mechanism 140 which is not illustrated in FIGS. 5A, 5B and 5C descends a movable portion 141b of the housing securing jig 141 which has been withdrawn at a predetermined withdrawal position, not illustrated, toward the projection 5b from thereabove vertically, to bring it into contact with the projection 5b, as indicated by an arrow AR1. Thus, as illustrated in FIG. 5C, the housing securing jig 141 secures, through pinching, the projection 5b of the housing 5. Namely, this realizes a state where the tubular body 30 including the housing 5 is secured by the housing securing jig 141.

Further, the transfer of the washer 7, the ceramic supporters 8 and the powder compacts 9, and the fitting of them to the element dummy 121, and the subsequent fitting of the tubular body 30 onto the outer peripheries of these annularly-mounted members, using the annularly-mounted member transfer mechanism 130, may be also realized in an aspect as follows. That is, the annularly-mounted member transfer mechanism 130 may include different transfer arms and the like which are formed from respective materials to have respective configurations, depending on the shapes and the materials of the respective members. Thus, the annularly-mounted member transfer mechanism 130 may use these transfer arms and the like, for realizing the aforementioned transfer and fitting.

Further, the shapes of the supporting portion 141a and the movable portion 141b which constitute the housing securing jig 141 are not particularly limited, provided that they can secure, through pinching, the projection 5b of the housing 5 in the vertically upward/downward direction. For example, the supporting portion 141a and the movable portion 141b may be each formed from a pair of members having a symmetric shape or from a single member with a C shape or a U shape in a plane view. Also, the supporting portion 141a and the movable portion 141b may have respective different shapes.

Figure 6A:
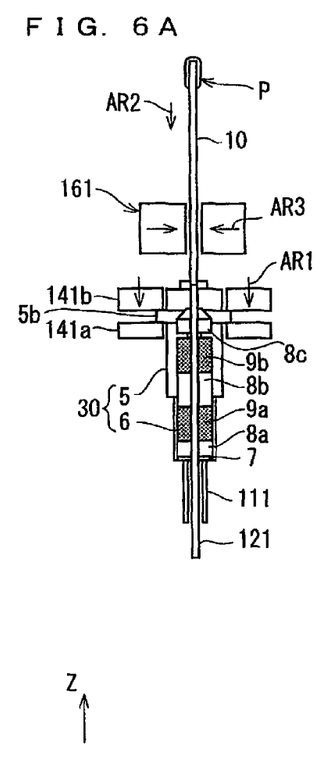

After the tubular body 30 including the housing 5 was secured in the aforementioned manner, subsequently, the sensor element 10 is placed in contact with the element dummy 121, at a position where it aligns with the element dummy 121 in a single straight line, in such an attitude that its end portion (the first tip 10*a*) provided with the protection film P is at the upper end side, as illustrated in FIG. 6A. This placement of the sensor element 10 can be realized as follows. That is, the element transfer mechanism 150 which is not illustrated in FIGS. 6A, 6B and 6C transfers the sensor element 10 which has been preliminarily carried therein from the outside of the apparatus and has been on standby at an element standby part 151, to above the element dummy 121, in such a manner as not to come into contact with the protection film P. Further, the element transfer mechanism 150 descends it vertically above the element dummy 121, as indicated by an arrow AR2 in FIG. 6A, and brings it into contact with the upper end of the element dummy 121. The element transfer mechanism 150 holds the sensor element 10 at this position. At this time, the element transfer mechanism 150 functions as element placing means for placing the sensor element 10 in contact with the upper end portion of the element dummy 121.

The concrete structure of the element transfer mechanism 150 is not particularly limited, as long as it can preferably transfer and hold the sensor element 10 in such a way as not to come into contact with the protection film P.

Figure 6B:
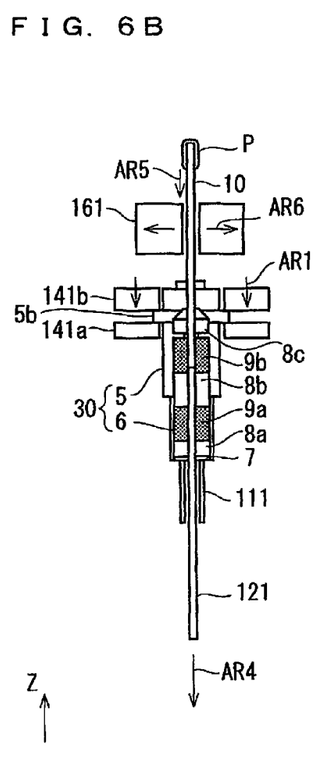
Figure 6C:
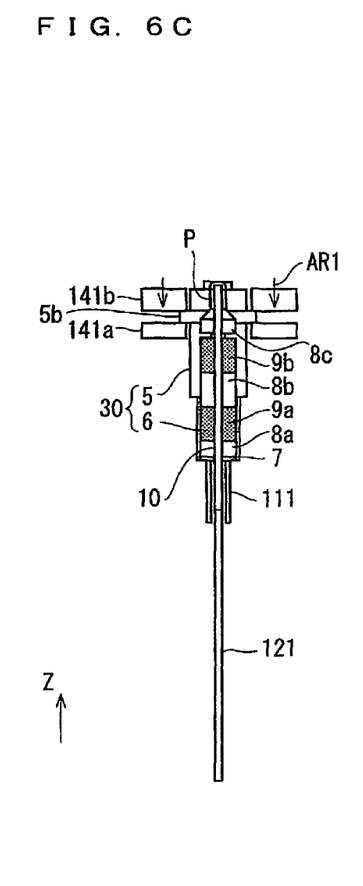

After the sensor element 10 was placed as described above, the element guide jig driving mechanism 160 which is not illustrated in FIGS. 6A, 6B and 6C is driven, and then, the element guide jig 161 is placed at a position beside the sensor element 10, as indicated by an arrow AR3 in FIG. 6A. The element guide jig 161 is placed for supporting and guiding the sensor element 10, when the sensor element 10 is descended downwardly vertically, in the following processing. Therefore, the surface of the element guide jig 161 which is faced to the sensor element 10 is formed from a material which does not injure the sensor element 10 even when the sensor element 10 comes into contact therewith, and this surface of the element guide jig 161 is placed to extend in the vertical direction at a position where it is proximal to or in contact with the sensor element 10.

When the element guide jig 161 is placed, the holding of the sensor element 10 by the element transfer mechanism 150 is released, which brings the sensor element 10 into a state of being supported at its lower end portion (the second tip end portion 10*b*) by the element dummy 121. Further, the dummy elevating mechanism 120 which is not illustrated in FIGS. 6A, 6B and 6C is activated again and, thus, the element dummy 121 is descended downwardly vertically, as indicated by an arrow AR4 in FIG. 6B. Then, in response to this descending, the sensor element 10 having been supported at its lower end portion (the second tip end portion 10*b*) by the element dummy 121 is also descended downwardly vertically. Thus, within the through holes in the annularly-mounted members, the element dummy 121 and the sensor element 10 are successively interchanged with each other. This consequently realizes a state where the annularly-mounted members are annularly mounted to the sensor element 10. At this time, the dummy elevating mechanism 121 functions as element fitting means for fitting the through holes in the annularly-mounted members to the sensor element 10.

In this aspect, the annularly-mounted members are consistently in the state of being annularly mounted to the element dummy 121 or the sensor element 10. This can preferably inhibit the occurrence of malfunctions that the annularly-mounted members are displaced to make it impossible to assemble the sensor element 10 therein.

At a time when this descending of the sensor element 10 has proceeded to some extent, and the sensor element 10 has come to descend downwardly vertically even without the supporting and the guiding by the element guide jig 161, the element guide jig driving mechanism 160 is activated again to separate the element guide jig 161 from the sensor element 10, as indicated by an arrow AR6 in FIG. 6B. This is for preventing the protection film P from coming into contact with the element guide jig 161.

The descending of the sensor element 10 by descending the element dummy 121 is performed, until the sensor element 10 penetrates through the washer 7 and, also, the vicinity of the upper end portion (the first tip 10*a*) of the sensor element 10 reaches the position of the upper end of the housing 5. It is preferable that the degree of protrusion of the upper end portion of the sensor element 10 from the housing 5 is adjusted, in detail, such that the degree of the protrusion thereof is preferable when the gas sensor 1 is finally obtained.

Figure 7A:
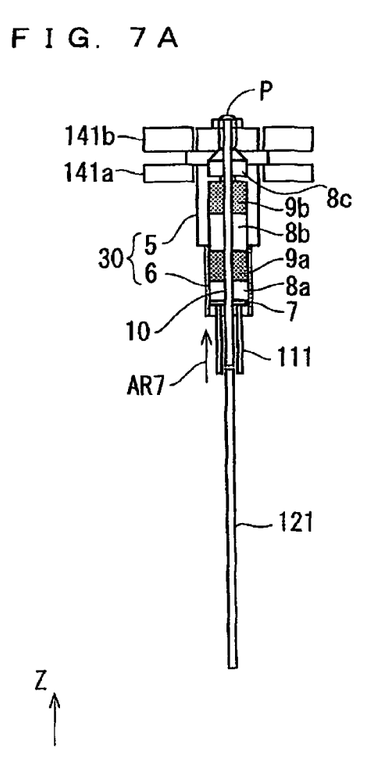
Figure 7B:
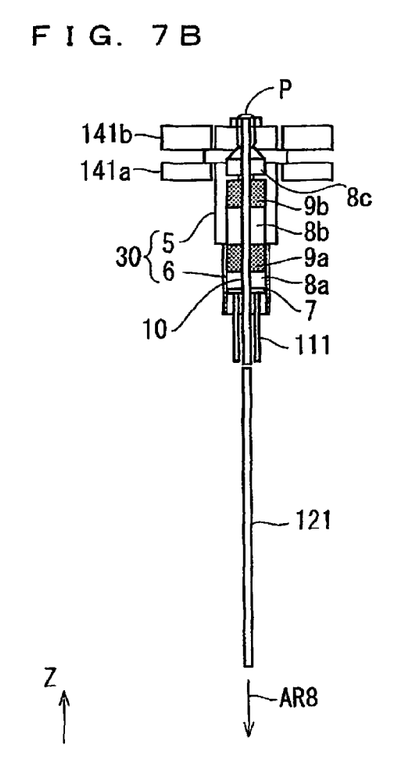

Subsequently, the sealing-jig elevating mechanism 110 which is not illustrated in FIGS. 7A and 7B is activated, again, to ascend the sealing jig 111 as indicated by an arrow AR7 in FIG. 7A, thereby pressing the entire annularly-mounted members, upwardly vertically, at their lower end portion side. Then, the powder compacts 9 (9*a* and 9*b*) are compressed to a predetermined thickness, thereby attaining sealing between the first tip 10*a* including the gas inlet port 11 and the like and the second tip 10*b* including the connection terminal 13 of the cable C and the like, in the sensor element 10, within the tubular body 30. This secures the hermeticity between the measurement gas space and the reference gas space in the gas sensor 1. At this time, the sealing jig 111 and the sealing-jig elevating mechanism 110 function as pressing means for compressing the powder compacts.

This compression results in a state where the upper end of the element dummy 121 and the lower end of the sensor element 10 are separated from each other, as illustrated in FIG. 7A. After this state has been attained, as indicated by an arrow AR8 in FIG. 7B the dummy elevating mechanism 120 which is not illustrated in FIGS. 7A and 7B further descends the element dummy 121, thereby withdrawing the element dummy 121 to a predetermined position.

Figure 8A:
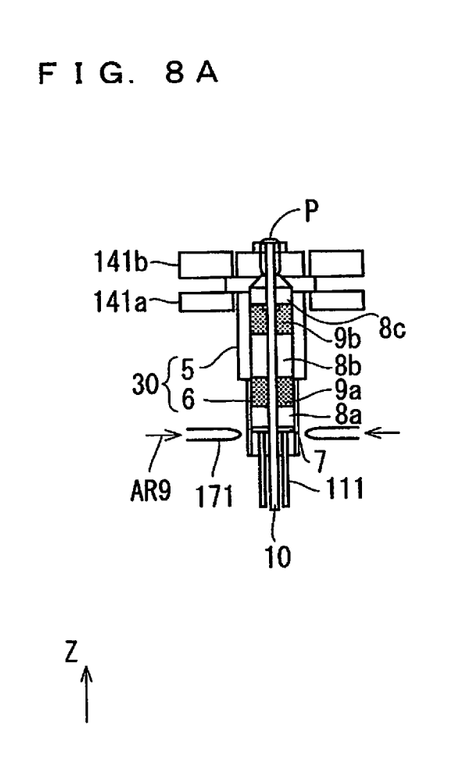
Figure 8B:
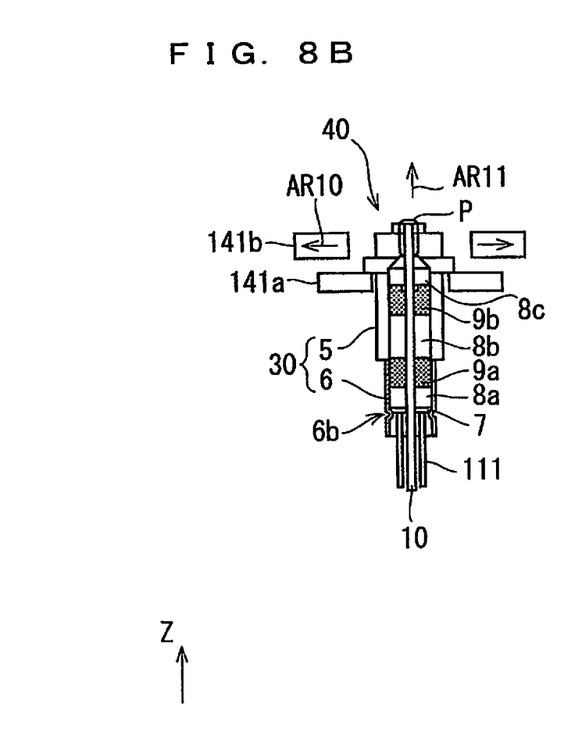

Subsequently, the swaging jig driving mechanism 170 which is not illustrated in FIGS. 8A and 8B is activated, so that the swaging jig 171 gets closer to the inner tube 6 laterally and swages the inner tube 6 at its outer periphery at a height position just below the washer 7, as indicated by an arrow AR9 in FIG. 8A. Since a space has been formed under the washer 7 within the inner tube 6 as a result of the aforementioned compression of the powder compacts 9 by the sealing jig 111, this swaging results in preferable formation of the concave portion 6*b* at a position just below the washer 7, in the inner tube 6, as illustrated in FIG. 8B. Due to the formation of this concave portion 6*b*, it is possible to prevent disengagements of the annularly-mounted members, when the assembled product 40 is finally extracted at its upper side. This realizes the engagement of the annularly-mounted members with the inside of the tubular body 30, as described above. At this time, the swaging jig 171 and the swaging jig driving mechanism 170 function as swaging means for forming the concave portion 6*b* for engaging the annularly-mounted members with the inner tube 6 which forms the tubular body 30.

With the formation of the aforementioned concave portion 6*b*, the assembled product 40 has been finished. After the formation of this concave portion 6*b*, the housing securing jig driving mechanism 140 which is not illustrated in FIGS. 8A and 8B is activated, again, to withdraw the movable portion 141b of the housing securing jig 141 to a predetermined withdrawal position, as indicated by an arrow AR10 in FIGS. 8A and 8B. This realizes a state where the assembled product 40 is supported from therebelow by the sealing jig 111 and the supporting portion 141a of the housing securing jig 141. Subsequently, the assembled-member transfer mechanism 180 which is not illustrated in FIGS. 8A and 8B pulls the assembled member 40 upwardly vertically as indicated by an arrow AR11 in FIGS. 8A and 8B and, further, transfers it to the assembled-member standby part 181. The concrete structure of the assembled-member transfer mechanism 180 is not particularly limited, as long as it is capable of preferably performing such pulling up and transferring of the assembled member 40.

With that, the series of assembling procedure with the assembling apparatus 100 has been completed. When another assembled product 40 should be assembled subsequently, the same procedure is repeated from the state illustrated in FIG. 5A. Further, the resultant assembled product 40 is supplied to the outside of the assembling apparatus 100, and the first cover 2, the fixing bolt 3 and the second cover 4 are attached thereto. Thus, the gas sensor 1 (the main body thereof) 1 has been finished.

With the procedure for assembling the assembled member which is realized according to the present preferred embodiment, the annularly-mounted members are consistently in the state of being annularly mounted to the element dummy or the sensor element. This can preferably inhibit the occurrence of malfunctions that the annularly-mounted members are displaced to make it impossible to assemble the sensor element therein.

Further, the sensor element is not passed through the through holes in the annularly-mounted members, at its first tip provided with the opening portion. Therefore, even in cases of using the sensor element provided with the protection film at its first tip, it is possible to preferably perform assembling thereof.

While the invention has been shown and described in detail, the foregoing description is in all aspects illustrative and not restrictive. It is therefore understood that numerous modifications and variations can be devised without departing from the scope of the invention.

What is claimed is:

1. A gas sensor assembling method comprising:
   placing an element dummy having a shape similar to that of a sensor element such that it has a longitudinal direction in a vertical direction, said sensor element having an elongated shape mainly composed of a ceramic;
   fitting a through hole in an annularly-mounted member to said element dummy from above vertically, said annularly-mounted member having a disk shape or a cylindrical shape, and said through hole having a shape corresponding to a cross-sectional shape of said sensor element;
   fitting a tubular body to an outer periphery of said annularly-mounted member from above vertically;
   placing said sensor element in contact with an upper end portion of said element dummy on a single straight line; and
   descending said element dummy downwardly vertically for descending said sensor element and fitting said through hole in said annularly-mounted member to said sensor element.

2. The gas sensor assembling method according to claim 1, wherein
   said sensor element is provided with a protection film on a surface of its one end, and
   said sensor element is placed in contact with the upper end portion of said element dummy such that another end of said sensor element which is not provided with said protection film is supported by said element dummy.

3. The gas sensor assembling method according to claim 2, further comprising
   forming a concave portion for engaging said annularly-mounted member therewith, wherein the concave portion is formed after descending said element dummy downwardly vertically and fitting said through hole in said annularly-mounted member to said sensor element, and
   said tubular body is swaged at its lower end potion at a position just below said annularly-mounted member, at an outer periphery of said tubular body, for forming said concave portion.

4. The gas sensor assembling method according to claim 3, wherein
   fitting the through hole in the annularly-mounted member to said element dummy from above vertically comprises fitting two or more types of members including a powder compact made of a ceramic, as said annularly-mounted member, to said element dummy,
   said assembling method further comprises:
   pressing said annularly-mounted member at a lower end portion in the vertical direction upwardly vertically for compressing said powder compact after descending said element dummy downwardly vertically and fitting said through hole in said annularly-mounted member to said sensor element, and
   swaging a vacancy portion formed just beneath said annularly-mounted member within said tubular body.

5. The gas sensor assembling method according to claim 1, further comprising
   forming a concave portion for engaging said annularly-mounted member therewith, wherein said concave portion is formed after descending said element dummy downwardly vertically and fitting said through hole in said annularly-mounted member to said sensor element, and
   said tubular body is swaged at its lower end potion at a position just below said annularly-mounted member, at an outer periphery of said tubular body, for forming said concave portion.

6. The gas sensor assembling method according to claim 5, wherein
   fitting the through hole in the annularly-mounted member to said element dummy from above vertically comprises fitting two or more types of members including a powder compact made of a ceramic, as said annularly mounted member, to said element dummy,
   said assembling method further comprises:
   pressing said annularly-mounted member at a lower end portion in the vertical direction upwardly vertically for compressing said powder compact after descending said element dummy downwardly vertically and fitting said through hole in said annularly-mounted member to said sensor element, and
   swaging a vacancy portion formed just beneath said annularly-mounted member within said tubular body.

7. The gas sensor assembling method according to claim 6, wherein
fitting the through hole in the annularly-mounted member to said element dummy from above vertically comprises supporting said annularly-mounted member from therebelow, by a jig for use in pressing said annularly-mounted member at the lower end portion.

8. The gas sensor assembling method according to claim 7, wherein
fitting the through hole in the annularly-mounted member to said element dummy from above vertically comprises supporting said annularly-mounted member from therebelow, by a jig for use in pressing said annularly-mounted member at the lower end portion.

9. The gas sensor assembling method according to claim 1, wherein
the annularly-mounted member is consistently in a state of being annularly mounted to the element dummy or the sensor element.

10. A gas sensor assembling apparatus comprising:
an element dummy having a shape similar to that of a sensor element, said sensor element having an elongated shape mainly composed of a ceramic;
a dummy placing component for placing said element dummy such that it has a longitudinal direction in a vertical direction;
an annularly-mounted member fitting component for fitting a through hole in an annularly-mounted member to said element dummy from above vertically, said annularly-mounted member having a disk shape or a cylindrical shape, and said through hole having a shape corresponding to a cross-sectional shape of said sensor element;
a tubular-body fitting component for fitting a tubular body to an outer periphery of said annularly-mounted member from above vertically;
an element placing component for placing said sensor element in contact with an upper end portion of said element dummy on a single straight line; and
an element fitting component for descending said element dummy downwardly vertically for descending said sensor element and fitting said through hole in said annularly-mounted member to said sensor element.

11. The gas sensor assembling apparatus according to claim 10, wherein
when said sensor element is provided with a protection film on a surface of its one end, said element placing component places said sensor element, such that another end of said sensor element which is not provided with said protection film is supported by said element dummy.

12. The gas sensor assembling apparatus according to claim 11, further comprising
a swaging component for forming a concave portion for engaging said annularly-mounted member therewith, in said tubular body fitted to the outer periphery of said annularly-mounted member, wherein said swaging component is adapted to swage said tubular body at its lower end potion at a position just below said annularly-mounted member, at an outer periphery of said tubular body, for forming said concave portion.

13. The gas sensor assembling apparatus according to claim 12, wherein
a pressing component for pressing said annularly-mounted member at its lower end portion in the vertical direction upwardly vertically for compressing a powder compact, when two or more types of members including said powder compact made of a ceramic, as said annularly-mounted member, are fitted to said element dummy,
said swaging component is adapted to apply swaging to a vacancy portion formed just beneath said annularly-mounted member within said tubular body by said pressing component.

14. The gas sensor assembling apparatus according to claim 13, wherein
said pressing component also serves as a supporting component for supporting said annularly-mounted member having been fitted, from therebelow, with a jig for use in pressing said annularly-mounted member.

15. The gas sensor assembling apparatus according to claim 10, further comprising
a swaging component for forming a concave portion for engaging said annularly-mounted member therewith, in said tubular body fitted to the outer periphery of said annularly-mounted member, wherein said swaging component is adapted to swage said tubular body at its lower end potion at a position just below said annularly-mounted member, at an outer periphery of said tubular body, for forming said concave portion.

16. The gas sensor assembling apparatus according to claim 15, wherein
a pressing component for pressing said annularly-mounted member at a lower end portion in the vertical direction upwardly vertically for compressing a powder compact, when two or more types of members including said powder compact made of a ceramic, as said annularly mounted member, are fitted to said element dummy,
said swaging component is adapted to apply swaging to a vacancy portion formed just beneath said annularly-mounted member within said tubular body by the pressing component.

17. The gas sensor assembling apparatus according to claim 16, wherein
said pressing component also serves as a supporting component for supporting said annularly-mounted member having been fitted, from therebelow, with a jig for use in pressing said annularly-mounted member.

18. The gas sensor assembling apparatus according to claim 10, wherein
the annularly-mounted member is consistently in a state of being annularly mounted to the element dummy or the sensor element.

* * * * *